(12) United States Patent
Tomonaga et al.

(10) Patent No.: US 12,723,021 B2
(45) Date of Patent: Sep. 1, 2026

(54) METHOD FOR PRODUCING TRISULFIDE COMPOUND OR SELENOTRISULFIDE COMPOUND

(71) Applicant: Kyowa Pharma Chemical Co., Ltd., Takaoka (JP)

(72) Inventors: Shoichiro Tomonaga, Takaoka (JP); Ikumi Shimokawa, Takaoka (JP)

(73) Assignee: Kyowa Pharma Chemical Co., Ltd., Takaoka (JP)

(*) Notice: Subject to any disclaimer, the term of this patent is extended or adjusted under 35 U.S.C. 154(b) by 936 days.

(21) Appl. No.: 17/906,837

(22) PCT Filed: Mar. 24, 2021

(86) PCT No.: PCT/JP2021/012296

§ 371 (c)(1), (2) Date: Sep. 20, 2022

(87) PCT Pub. No.: WO2021/200487

PCT Pub. Date: Oct. 7, 2021

(65) Prior Publication Data

US 2023/0192604 A1 Jun. 22, 2023

(30) Foreign Application Priority Data

Mar. 31, 2020 (JP) ................................ 2020-064262

(51) Int. Cl.

| | |
|---|---|
| ***C07C 319/24*** | (2006.01) |
| ***C07C 323/59*** | (2006.01) |
| ***C07C 323/60*** | (2006.01) |
| ***C07C 391/00*** | (2006.01) |
| ***C07D 341/00*** | (2006.01) |

(52) U.S. Cl.

CPC .......... *C07C 319/24* (2013.01); *C07C 323/59* (2013.01); *C07C 323/60* (2013.01); *C07C 391/00* (2013.01); *C07D 341/00* (2013.01)

(58) Field of Classification Search

USPC ........................................................... 568/21

See application file for complete search history.

(56) References Cited

U.S. PATENT DOCUMENTS

| | | | | |
|---|---|---|---|---|
| 4,614,281 | A | 9/1986 | Kihara et al. | |
| 4,614,821 | A * | 9/1986 | Kihara | C07D 341/00 548/146 |
| 6,187,960 | B1 * | 2/2001 | Shaw | C07C 319/24 568/21 |
| 2020/0079818 | A1 | 3/2020 | Fujimoto et al. | |

FOREIGN PATENT DOCUMENTS

| | | | |
|---|---|---|---|
| CN | 107652264 | A | 2/2018 |
| CZ | 2014-319 | A3 | 11/2015 |
| JP | S60-094979 | A | 5/1985 |
| WO | WO 2018/117186 | A1 | 6/2018 |

OTHER PUBLICATIONS

Ryan et al., "Preparation of Dithioselenides via A Selenium Transfer Reagent," *Tetrahedron Letters*, 38(51): 8829-8832 (1997).

Banerjee, "S-Ethyl Ethanethiosulfinate," *e-EROS Encyclopedia of Reagents for Organic Synthesis*, pp. 1-3 (2007).

Chemical Society of Japan, "New Experimental Chemistry Course 14: Synthesis and Reactions of Organic Compounds III" (Maruzen Inc.), Section 8.4.2 (Synthesis by Thiol Oxidation Reaction), pp. 1736-1738 (1978).

Ishii, "Syntheses and Properties of vic-Disulfoxides," *Journal of Synthetic Organic Chemistry*, 64(4): 51-61 (2006).

Izmest'ev et al., "Oxidative Transformations of Diisobornyl Disulfide," *Russian Chemical Bulletin International Edition*, 63(9): 2067-2073 (2014).

Kice et al., "Mechanisms of the Reaction of Thiols with Selenite," *Journal of the American Chemical Society*, 102(13): 4448-4455 (1980).

Moutiez et al., "Reduction of a Trisulfide Derivative of Glutathione by Glutathione Reductase," *Biochem. Biophys. Res. Commun.*, 202(3): 1380-1386 (1994).

Japan Patent Office, International Search Report in International Patent Application No. PCT/JP2021/012296 (May 25, 2021).

Japan Patent Office, International Preliminary Report on Patentability in International Patent Application No. PCT/JP2021/012296 (Oct. 13, 2022).

Capozzi et al., "Silicon in Organosulphur Chemistry. Part 1. Synthesis of Trisulphides," *Tetrahedron Letters*, 30(22): 2991-2994 (1989).

Chauvin et al., "The Antioxidant Activity of Polysulfides: It's Radical!," *Chem. Sci.*, 10(19): 4999-5010 (2019).

Lezina et al., "Reaction of Monoterpene Hydroxy Thiols with Chlorine Dioxide," *Russian Journal of Organic Chemistry*, 51(10): 1359-1367 (2015).

Ganther, "Reduction of the Selenotrisulfide Derivative of Glutathione to a Persulfide Analog by Glutathione Reductase," *Biochemistry*, 10(22): 4089-4098 (1971).

European Patent Office, Extended European Search Report in European Patent Application No. 21781393.0 (Apr. 29, 2024).

Hondal et al., "Selenocysteine in Thiol/Disulfide-Like Exchange Reactions," Antioxid. Redox Signal., 18(13): 1675-1689 (2013).

Intellectual Property India, Examination Report in Indian Patent Application No. 202247053424 (Nov. 6, 2025).

*Primary Examiner* — Ana Z Muresan

(74) *Attorney, Agent, or Firm* — Leydig, Voit & Mayer, Ltd.

(57) ABSTRACT

Disclosed is a method for producing a trisulfide compound or a selenotrisulfide compound. This production method includes: a step for oxidizing a disulfide compound with an oxidizing agent to obtain a sulfoxide compound; and a step for reacting the sulfoxide compound that has been obtained with a source of sulfur or a source of selenium to obtain a trisulfide compound or a selenotrisulfide compound.

4 Claims, No Drawings

METHOD FOR PRODUCING TRISULFIDE COMPOUND OR SELENOTRISULFIDE COMPOUND

TECHNICAL FIELD

The present invention relates to a method for producing a trisulfide compound or a selenotrisulfide compound.

BACKGROUND ART

A compound having a covalent bond structure consisting of three sulfur atoms (—S—S—S—) is called a trisulfide compound. Among trisulfide compounds, there are compounds used as flavors such as dimethyl trisulfide and dipropyl trisulfide and compounds expected to be an antioxidant component such as glutathione trisulfide.

Methods disclosed in Patent Literatures 1 and 2 and Non-Patent Literature 1 are known as methods for producing trisulfide compounds.

A compound having a covalent bond structure in which a sulfur atom in the center of trisulfide is replaced with a selenium atom (—S—Se—S—) is called a selenotrisulfide compound. Among selenotrisulfide compounds, there are compounds having an anticancer activity such as glutathione selenotrisulfide, and selenotrisulfide compounds are attracting attention as pharmaceutical products.

CITATION LIST

Patent Literature

[Patent Literature 1] CN 107652264 A

[Patent Literature 2] WO 2018/117186

Non-Patent Literature

[Non-Patent Literature 1] Moutiez et al., "Reduction of a trisulfide derivative of glutathione by glutathione reductase", Biochem. Biophys. Res. Commun., vol. 202, 1380-1386, 1994

SUMMARY OF INVENTION

Technical Problem

An object of the present invention is to provide a method for producing a trisulfide compound or a selenotrisulfide compound.

Solution to Problem

The present inventors have made diligent efforts to solve the above-described problem. As a result, they have found that a trisulfide compound or a selenotrisulfide compound can be obtained via a sulfoxide compound by an oxidation reaction of a disulfide compound or a thiol compound, thus leading to realization of the present invention.

That is, the present invention relates to (1) to (14) below.

(1) A method for producing a trisulfide compound or a selenotrisulfide compound, comprising:

oxidizing a disulfide compound with an oxidizing agent to obtain a sulfoxide compound; and allowing the obtained sulfoxide compound to react with a sulfur source or a selenium source to obtain a trisulfide compound or a selenotrisulfide compound.

(2) The method according to (1), wherein obtaining the sulfoxide compound and obtaining the trisulfide compound are performed in a one-pot reaction.

(3) The method according to (1) or (2), wherein the oxidizing agent is potassium peroxymonosulfate, peracetic acid, hydrogen peroxide, hydrogen peroxide with methyltrioxorhenium, or sodium periodate.

(4) The method according to any one of (1) to (3), wherein the sulfur source is sodium sulfide, potassium sulfide, sodium hydrosulfide, potassium hydrosulfide, or hydrogen sulfide and the selenium source is sodium selenide, potassium selenide, sodium hydroselenide, potassium hydroselenide, or hydrogen selenide.

(5) The method according to any one of (1) to (4), wherein the disulfide compound is a compound represented by $R^1$—S—S—$R^2$, wherein $R^1$ and $R^2$ may be the same or different, and each represents an alkyl group optionally substituted with one or more substituents selected from Substituent Group A, Substituent Group A consists of a halogen atom, a hydroxy group, an amino group optionally substituted with one or more substituents selected from Substituent Group B, and an oxo group, and Substituent Group B consists of an alkyl group optionally substituted with one or more substituents selected from the group consisting of a hydroxy group, an amino group and an oxo group, and an acetyl group.

(6) The method according to any one of (1) to (4), wherein the disulfide compound is a compound represented by $R^3$—S—S—$R^4$, wherein $R^3$ and $R^4$ may be the same or different, and each represents a group in which an SH group is removed from cysteine optionally protected by a protective group or a group in which an SH group is removed from a cysteine-containing peptide optionally protected by a protective group.

(7) A method for producing a trisulfide compound or a selenotrisulfide compound, comprising:

oxidizing a thiol compound with an oxidizing agent to obtain a sulfoxide compound; and allowing the obtained sulfoxide compound to react with a sulfur source or a selenium source to obtain a trisulfide compound or a selenotrisulfide compound.

(8) The method according to (7), wherein obtaining the sulfoxide compound and obtaining the trisulfide compound are performed in a one-pot reaction.

(9) The method according to (7) or (8), wherein the oxidizing agent is potassium peroxymonosulfate, peracetic acid, hydrogen peroxide, hydrogen peroxide with methyltrioxorhenium, or sodium periodate.

(10) The method according to any one of (7) to (9), wherein the sulfur source is sodium sulfide, potassium sulfide, sodium hydrosulfide, potassium hydrosulfide, or hydrogen sulfide and the selenium source is sodium selenide, potassium selenide, sodium hydroselenide, potassium hydroselenide, or hydrogen selenide.

(11) The method according to any one of (7) to (10), wherein the thiol compound is a compound represented by $R^1$—SH, wherein $R^1$ represents an alkyl group optionally substituted with one or more substituents selected from Substituent Group A, Substituent Group A consists of a halogen atom, a hydroxy group, an amino group optionally substituted with one or more substituents selected from Substituent Group B, and an oxo group, and Substituent Group B consists of an alkyl group optionally substituted with one or more substituents selected from the group consisting of a hydroxy group, an amino group and an oxo group, and an acetyl group.

(12) The method according to any one of (7) to (10), wherein the thiol compounds are a compound represented by $R^1$—SH and a compound represented by $R^2$—SH, wherein $R^1$ and $R^2$ are different and each represents an alkyl group optionally substituted with one or more substituents selected from Substituent Group A, Substituent Group A consists of a halogen atom, a hydroxy group, an amino group optionally substituted with one or more substituents selected from Substituent Group B, and an oxo group, and Substituent Group B consists of an alkyl group optionally substituted with one or more substituents selected from the group consisting of a hydroxy group, an amino group and an oxo group, and an acetyl group.

(13) The method according to any one of (7) to (10), wherein the thiol compound is a compound represented by $R^3$—SH, wherein $R^3$ represents a group in which an SH group is removed from cysteine optionally protected by a protective group or a group in which an SH group is removed from a cysteine-containing peptide optionally protected by a protective group.

(14) The method according to any one of (7) to (10), wherein the thiol compounds are a compound represented by $R^3$—SH and a compound represented $R^4$—SH, wherein $R^3$ and $R^4$ are different and each represents a group in which an SH group is removed from cysteine optionally protected by a protective group or a group in which an SH group is removed from a cysteine-containing peptide optionally protected by a protective group.

Advantageous Effects of Invention

The method for producing a trisulfide compound or a selenotrisulfide compound according to the present invention is safe and inexpensive.

DESCRIPTION OF EMBODIMENTS

A method for producing a trisulfide compound or a selenotrisulfide compound according to one embodiment of the present invention includes: a step of oxidizing a disulfide compound with an oxidizing agent to obtain a sulfoxide compound (Step 1); and a step of allowing the obtained sulfoxide compound to react with a sulfur source or a selenium source to obtain a trisulfide compound or a selenotrisulfide compound (Step 2).

In the above-described production method, Step 1 and Step 2 may be performed in a one-pot reaction without isolating the sulfoxide compound.

A solvent used in Step 1 is not particularly limited as long as it dissolves a disulfide compound and an oxidizing agent and does not inhibit the oxidation reaction. Examples of such solvents include water, a sulfuric acid aqueous solution, an ethanol aqueous solution, and an acetonitrile aqueous solution, and water is preferable. The amount of solvent used in Step 1 can be 1 mL to 500 mL, preferably 10 mL to 20 mL with respect to 1 grain of the disulfide compound.

Examples of oxidizing agents used in Step 1 include potassium peroxymonosulfate (available under a trade name such as Oxone (registered trademark) or the like), peracetic acid, hydrogen peroxide, and sodium periodate. Hydrogen peroxide may be used with a catalytic amount of methyltrioxorhenium. Potassium peroxymonosulfate is a preferred oxidizing agent from the viewpoints of safety and costs. The amount of oxidizing agent used can be 0.8 equivalents to 2.0 equivalents, preferably 1.0 equivalent to 1.3 equivalents with respect to 1 equivalent of the disulfide compound.

The reaction temperature in Step 1 can be −20° C. to 30° C., preferably −5° C. to 5° C.

The reaction time of Step 1 can be 5 minutes to 24 hours, preferably 0.5 hours to 2 hours.

A solvent used in Step 2 is not particularly limited as long as it dissolves a sulfoxide compound and a sulfur source or a selenium source and does not inhibit the reaction thereafter. Examples of such solvents include water, a sulfuric acid aqueous solution, an ethanol aqueous solution, and an acetonitrile aqueous solution, and water is preferable. The amount of solvent used in Step 2 can be 1 mL to 500 mL, preferably 10 mL to 20 mL with respect to 1 grain of the sulfoxide compound.

Examples of sulfur sources used in Step 2 include sodium sulfide, potassium sulfide, sodium hydrosulfide, potassium hydrosulfide, and hydrogen sulfide. The amount of sulfur source used can be 0.5 equivalents to 4.0 equivalents, preferably 0.9 equivalents to 1.2 equivalents with respect to 1 equivalent of the sulfoxide compound. Examples of selenium sources used in Step 2 include sodium selenide, potassium selenide, sodium hydroselenide, potassium hydroselenide, and hydrogen selenide. The amount of selenium source used can be 0.5 equivalents to 4.0 equivalents, preferably 0.9 equivalents to 1.2 equivalents with respect to 1 equivalent of the sulfoxide compound.

The reaction temperature in Step 2 can be −20° C. to 30° C., preferably −5° C. to 25° C.

The reaction time of Step 2 can be 10 minutes to 2 days, preferably 0.5 hours to 2 hours.

In a case where Step 1 and Step 2 are performed in a one-pot reaction, examples of reaction solvents include water, a sulfuric acid aqueous solution, an ethanol aqueous solution, and an acetonitrile aqueous solution, and water is preferable, and the amount of solvent can be 1 mL to 500 mL, preferably 10 mL to 20 mL with respect to 1 grain of a disulfide compound. Examples of oxidizing agents used include potassium peroxymonosulfate, peracetic acid, hydrogen peroxide (which may be used with a catalytic amount of methyltrioxorhenium), and sodium periodate, preferably potassium peroxymonosulfate. The amount of oxidizing agent used can be 0.8 equivalents to 2.0 equivalents, preferably 1.0 equivalent to 1.3 equivalents with respect to 1 equivalent of a disulfide compound. The amount of oxidizing agent used can be 0.8 equivalents to 2.0 equivalents, preferably 1.0 equivalent to 1.3 equivalents with respect to 1 equivalent of the disulfide compound. Examples of sulfur sources used include sodium sulfide, potassium sulfide, sodium hydrosulfide, potassium hydrosulfide, and hydrogen sulfide. The amount of sulfur source used can be 0.5 equivalents to 4.0 equivalents, preferably 0.9 equivalents to 1.2 equivalents with respect to 1 equivalent of a disulfide compound. Examples of selenium sources used include sodium selenide, potassium selenide, sodium hydroselenide, potassium hydroselenide, and hydrogen selenide. The amount of selenium source used can be 0.5 equivalents to 4.0 equivalents, preferably 0.9 equivalents to 1.2 equivalents with respect to 1 equivalent of a disulfide compound. The reaction temperature can be −20° C. to 30°

C., preferably −5° C. to 25° C. The reaction time can be 15 minutes to 2 days, preferably 1 hour to 4 hours.

In addition to Step 1 and Step 2, a step of protecting functional groups such as a hydroxy group, a carbonyl group, an amino group, and a carboxy group and a step of deprotecting the protected functional groups may be included as necessary. Protective groups for these functional groups and protection and deprotection reactions are well known to those skilled in the art, and appropriate protective groups and protection and deprotection reactions can be selected with reference to "Greene's Protective Groups in Organic Synthesis."

Examples of disulfide compounds include a compound represented by $R^1$—S—S—$R^2$. $R^1$ and $R^2$ may be the same (that is, symmetric disulfide compounds) and may be different (that is, asymmetric disulfide compounds). $R^1$ and $R^2$ may together form groups (that is, cyclic disulfide compounds) described below.

$R^1$ and $R^2$ each represents an alkyl group optionally substituted with one or more substituents selected from Substituent Group A. Substituent Group A consists of a halogen atom, a hydroxy group, an amino group optionally substituted with one or more substituents selected from Substituent Group B, and an oxo group. Substituent Group B consists of an alkyl group optionally substituted with one or more substituents selected from the group consisting of a hydroxy group, an amino group and an oxo group, and an acetyl group The alkyl group may have 1 to 6 carbon atoms, and examples thereof include a methyl group, an ethyl group, a propan-1-yl group, a propan-2-yl group (isopropyl group), a butan-1-yl group, a butan-2-yl group, a pentan-1-yl group, a pentan-2-yl group, a pentan-3-yl group, a hexan-1-yl group, a hexan-2-yl group, and a 3-hexyl group.

In a case where the disulfide compound is a compound represented by $R^1$—S—S—$R^2$, a sulfoxide compound produced is a compound represented by $R^1$—S(═O)—S—$R^2$ or $R^1$—S—S(═O)—$R^2$, a trisulfide compound produced is a compound represented by $R^1$—S—S—S—$R^2$, and a selenotrisulfide compound produced is a compounds represented by $R^1$—S—Se—S—$R^2$.

Another example of disulfide compounds includes a compound represented by $R^3$—S—S—$R^4$. $R^3$ and $R^4$ may be the same (that is, symmetric disulfide compounds) and may be different (that is, asymmetric disulfide compounds). $R^3$ and $R^4$ may together form groups (that is, cyclic disulfide compounds) described below.

$R^3$ and $R^4$ each represents a group in which an SH group is removed from cysteine optionally protected by a protective group or a group in which an SH group is removed from a cysteine-containing peptide optionally protected by a protective group. The length of the peptide is not particularly limited but may be, for example, a peptide consisting of 2 to 10 amino acids, and is preferably a peptide consisting of 2 to 5 amino acids. Examples of cysteine protected by a protective group include cysteine in which a carboxy group and/or an amino group are protected, and specific examples thereof include N-acetylcysteine.

Examples of peptides protected by a protective group include a peptide in which a side chain having a C-terminal carboxy group, an N-terminal amino group and/or a reactive functional group (for example, an amino group in a lysine residue and a carboxy group in an aspartic acid residue and a glutamic acid residue) is protected.

In a case where the disulfide compound is a compound represented by $R^3$—S—S—$R^4$, a sulfoxide compound produced is a compound represented by $R^3$—S(═O)—S—$R^4$ or $R^3$—S—S(═O)—$R^3$, a trisulfide compound produced is a compound represented by $R^3$—S—S—S—$R^4$, and a selenotrisulfide compound produced is a compound represented by $R^3$—S—Se—S—$R^4$.

A method for producing a trisulfide compound or a selenotrisulfide compound according to another embodiment of the present invention includes: a step of oxidizing a thiol compound with an oxidizing agent to obtain a sulfoxide compound (Step 1'); and a step of allowing the obtained sulfoxide compound to react with a sulfur source or a selenium source to obtain a trisulfide compound or a selenotrisulfide compound (Step 2).

The above-described production method may be performed in a one-pot reaction without isolating the disulfide compound.

A solvent used in Step 1' is not particularly limited as long as it dissolves a thiol compound and an oxidizing agent and does not inhibit the oxidation reaction. Examples of such solvents include water, a sulfuric acid aqueous solution, an ethanol aqueous solution, and an acetonitrile aqueous solution, and water is preferable. The amount of solvent used in Step 1' can be 1 mL to 500 mL, preferably 10 mL to 20 mL with respect to 1 grain of the thiol compound.

Oxidizing agents used in Step 1' and the amount thereof are the same as those described in Step 1.

The reaction temperature in Step 1' can be −20° C. to 30° C., preferably −5° C. to 5° C.

The reaction time of Step 1' can be 10 minutes to 24 hours, preferably 0.5 hours to 2 hours.

In a case where Step 1 and Step 2 are performed in a one-pot reaction, examples of reaction solvents include water, a sulfuric acid aqueous solution, an ethanol aqueous solution, and an acetonitrile aqueous solution, and water is preferable, and the amount of solvent can be 1 mL to 500 mL, preferably 10 mL to 20 mL with respect to 1 gram of a thiol compound. Examples of oxidizing agents used include potassium peroxymonosulfate, peracetic acid, hydrogen peroxide (which may be used with a catalytic amount of methyltrioxorhenium), and sodium periodate, preferably potassium peroxymonosulfate. The amount of oxidizing agent used can be 0.8 equivalents to 2.0 equivalents, preferably 1.0 equivalent to 1.3 equivalents with respect to 1 equivalent of a thiol compound. The amount of oxidizing agent used can be set to 0.8 equivalents to 2.0 equivalents, preferably to 1 equivalent to 1.3 equivalents with respect to 1 equivalent of the thiol compound. Examples of sulfur sources used include sodium sulfide, potassium sulfide, sodium hydrosulfide, potassium hydrosulfide, and hydrogen sulfide. The amount of sulfur source used can be 0.5 equivalents to 4.0 equivalents, preferably 0.9 equivalents to 1.2 equivalents with respect to 1 equivalent of a thiol compound. Examples of selenium sources used include sodium selenide, potassium selenide, sodium hydroselenide, potassium hydroselenide, and hydrogen selenide. The amount of selenium source used can be 0.5 equivalents to 4.0 equivalents, preferably 0.9 equivalents to 1.2 equivalents with respect to 1 equivalent of a thiol compound. The reaction temperature can be −20° C. to 30° C., preferably −5° C. to 25° C. The reaction time can be 15 minutes to 2 days, preferably 1 hour to 4 hours.

In addition to Step 1' and Step 2, a step of protecting functional groups such as a hydroxy group, a carbonyl group, an amino group, and a carboxy group and a step of deprotecting the protected functional groups may be included as necessary. Protective groups for these functional groups and protection and deprotection reactions are well known to those skilled in the art, and appropriate protective groups and protection and deprotection reactions can be selected with reference to "Greene's Protective Groups in Organic Synthesis."

Examples of thiol compounds include a compound represented by $R^1$—SH. Two kinds of thiol compounds $R^1$—SH and $R^2$—SH may be used to perform a reaction. The definitions of $R^1$ and $R^2$ are as described above.

In a case where the thiol compound is a compound represented by $R^1$—SH, a sulfoxide compound produced is a compound represented by $R^1$—S(═O)—S—$R^1$, a trisulfide compound produced is a compound represented by $R^1$—S—S—S—$R^1$, and a selenotrisulfide compound produced is a compound represented by $R^1$—S—Se—S—$R^1$. In a case where the thiol compounds are a compound represented by $R^1$—SH and a compound represented by $R^2$—SH, a sulfoxide compound produced is any of a compound represented by $R^1$—S(═O)—S—$R^1$, a compounds represented by $R^2$—S(═O)—S—$R^2$, a compound represented by $R^1$—S(═O)—S—$R^2$, and a compound represented by $R^1$—S—S(═O)—$R^2$, or a mixture thereof. In a case of a mixture, a desired sulfoxide compound can be separated from the mixture as necessary. A trisulfide compound produced is any of a compound represented by $R^1$—S—S—S—$R^1$, a compound represented by $R^2$—S—S—S—$R^2$, and a compound represented by $R^1$—S—S—S—$R^2$, or a mixture thereof. A selenotrisulfide compound produced is any of a compound represented by $R^1$—S—Se—S—$R^1$, a compounds represented by $R^2$—S—Se—S—$R^2$, and a compound represented by $R^1$—S—Se—S—$R^2$, or a mixture thereof. In a case of a mixture, a desired trisulfide compound or a selenotrisulfide compound can be separated from the mixture as necessary.

Another example of thiol compounds includes a compound represented by $R^3$—SH. Two kinds of thiol compounds $R^3$—SH and $R^4$—SH may be used to perform a reaction. The definitions of $R^3$ and $R^4$ are as described above.

In a case where the thiol compound is a compound represented by $R^3$—SH, a sulfoxide compound produced is a compound represented by $R^3$—S(═O)—S—$R^3$, a trisulfide compound produced is a compound represented by $R^3$—S—S—S—$R^3$, and a selenotrisulfide compound produced is a compound represented by $R^3$—S—Se—S—$R^3$. In a case where the thiol compounds are a compound represented by $R^3$—SH and a compound represented by $R^4$—SH, a sulfoxide compound produced is any of a compound represented by $R^3$—S(═O)—S—$R^3$, a compound represented by $R^4$—S(═O)—S—$R^4$, a compound represented by $R^3$—S(═O)—S—$R^4$, and a compound represented by $R^3$—S—S(═O)—$R^4$, or a mixture thereof. In a case of a mixture, a desired sulfoxide compound can be separated from the mixture as necessary. A trisulfide compound produced is any of a compound represented by $R^3$—S—S—S—$R^3$, a compound represented by $R^4$—S—S—S—$R^4$, and a compound represented by $R^3$—S—S—S—$R^4$, or a mixture thereof. A selenotrisulfide compound produced is any of a compound represented by $R^3$—S—Se—S—$R^3$, a compound represented by $R^4$—S—Se—S—$R^4$, and a compound represented by $R^3$—S—Se—S—$R^4$, or a mixture thereof. In a case of a mixture, a desired trisulfide compound or a selenotrisulfide compound can be separated from the mixture as necessary.

EXAMPLES

Example 1

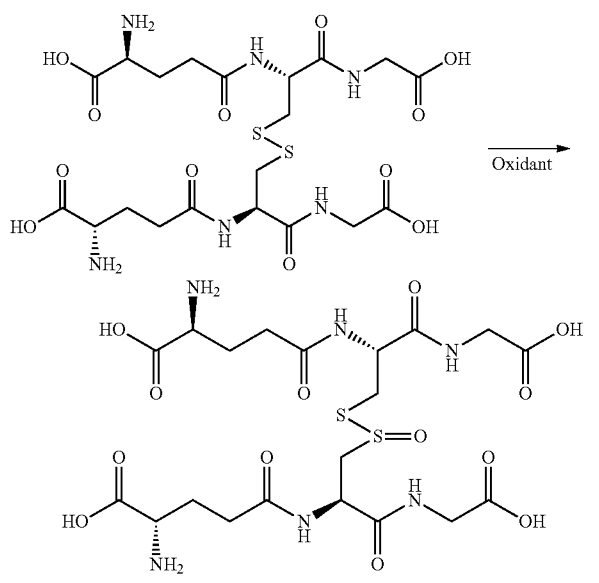

Oxidized glutathione (GSSG) and a sulfuric acid aqueous solution were added to a reaction container, and the temperature of this solution was adjusted. Peracetic acid ($AcO_2H$), hydrogen peroxide ($H_2O_2$), methyltrioxorhenium ($MeReO_3$), sodium periodate ($NaIO_4$), and Oxone (registered trademark) were added thereto at amounts shown in Table 1 to cause a reaction. Results of the purity of a product (GS(═O)SG) after the reaction measured by high-performance liquid chromatography (HPLC) and reaction conditions are shown in Table 1.

TABLE 1

| | Reaction conditions | | | | | | |
|---|---|---|---|---|---|---|---|
| Entry | GSSG (mmol) | Oxidizing agent (equivalent) | Additive | Concentration of sulfuric acid (amount of solvent) | Temperature | Time | GS(═O)SG HPLC area % |
| 1 | 13.9 | $AcO_2H$-1.3 | — | 1.0 mol/L (2.0 v/w) | 5° C. | 2 hours | 87 |
| 2 | 1.4 | $H_2O_2$-3.4 | — | 0.3 mol/L (4.5 v/w) | Ice bath → 20° C. | 22 hours | 42 |
| 3 | 1.4 | $H_2O_2$-1.2 | $MeReO_3$ (8 mol %) | 0.2 mol/L (6 v/w) | Ice bath | 10 minutes | 87 |

TABLE 1-continued

| | Reaction conditions | | | | | | |
|---|---|---|---|---|---|---|---|
| Entry | GSSG (mmol) | Oxidizing agent (equivalent) | Additive | Concentration of sulfuric acid (amount of solvent) | Temperature | Time | GS(═O)SG HPLC area % |
| 4 | 1.4 | $NaIO_4$-1.0 | — | 0.1 mol/L (7 v/w) | 5° C. | 40 minutes | 14 |
| 5 | 1.4 | Oxone ®-1.8 | — | 0.3 mol/L (6.5 v/w) | Ice bath | 1 hour | 86 |

*The equivalents and the solvent amounts are based on GSSG.

The HPLC conditions are as follows.
Detector: Ultraviolet absorptiometer (measurement wavelength: 220 nm)
Column: LiChrosorb RP-18 (Kanto Chemical Co., Inc., 4.0×250 mm, 5 μm)
Column temperature: Constant temperature around 40° C.
Mobile phase A: Phosphoric acid aqueous solution (pH 3)
Mobile phase B: Methanol
Mobile phase delivery: The mixing ratio of the mobile phase A and the mobile phase B is changed as follows to control the concentration gradient.

TABLE 2

| Time (minute) after injection | Mobile phase A (vol %) | Mobile phase B (vol %) |
|---|---|---|
| 0~5 | 100 | 0 |
| 5~15 | 100 → 50 | 0 → 50 |
| 15~20 | 50 | 50 |
| 20~21 | 50 → 100 | 50 → 0 |
| 21~30 | 100 | 0 |

Flow rate: 0.6 mL/min

Example 2

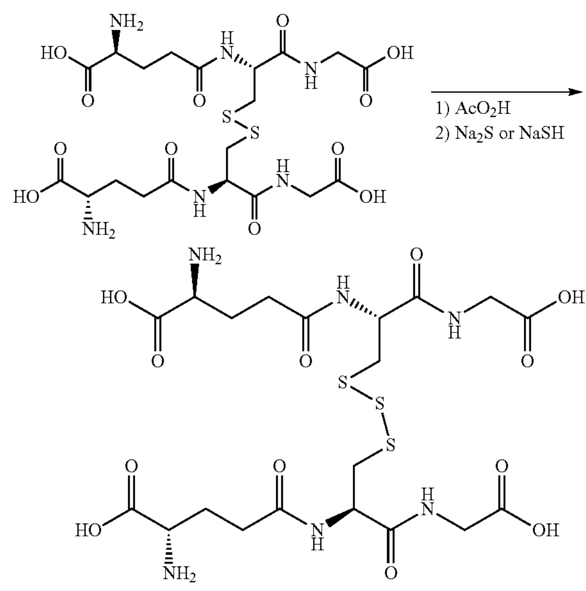

10 g (13.97 mmol) of oxidized glutathione (GSSG) and 20 mL of a 1 mol/L sulfuric acid aqueous solution were added to a reaction container and cooled in an ice bath. $AcO_2H$ (8.7% acetic acid solution, 15.8 g, 18.1 mmol) was added dropwise thereto to cause a reaction for about 2 hours. Subsequently, the temperature was raised to room temperature, and then each sulfur source shown in Table 2 was added thereto to cause a reaction for about 2 hours. After adding 27 mL of ethanol to the reaction mixture, 3 mL of a saturated sodium carbonate aqueous solution was added thereto. After filtering the slurry, crystals were washed with 20 mL of a 50% ethanol aqueous solution. The crystals collected by the filtration were dried under reduced pressure at room temperature to give glutathione trisulfide (product). Results and reaction conditions are shown in Table 3.

TABLE 3

| | Sulfur source | | | GSSSG | | |
|---|---|---|---|---|---|---|
| Entry | Reagent name | Charge amount (g) | mmol[1)] | Yield (g) | Yield (%) | HPLC area % |
| 1 | Sodium sulfide ($Na_2S$) | 3.8 | 16.8 | 7 | 73 | 95 |
| 2 | Sodium hydrosulfide (NaSH) | 2 | 21 | 6.4 | 68 | 92 |

[1)]$Na_2S$ and NaSH are calculated as nonahydrate and dihydrate, respectively.
* The yield is based on GSSG.

The HPLC conditions are the same as those described in Example 1.

Example 3

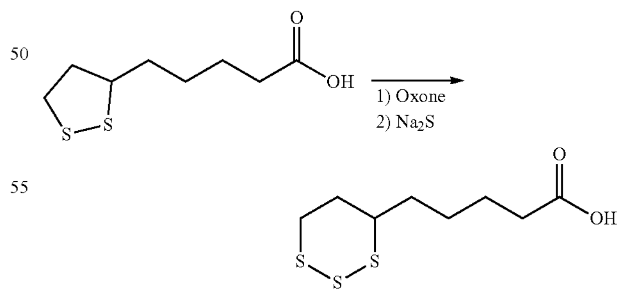

2.0 g (9.02 mmol) of α-lipoic acid and 40 mL of a 75% ethanol aqueous solution were added to a reaction container, and the mixture was cooled to an internal temperature of 0° C. 3.4 g (10.20 mmol) of Oxone (registered trademark) was added thereto to cause a reaction for about 2 hours. Inorganic salts in the reaction mixture were filtered and washed in 7 mL of ethanol. 5.8 g (24.1 mmol) of sodium sulfide nonahydrate was added to the filtrate to cause a reaction for about 1 hour. After 7 mL of a 3 mol/L sulfuric acid aqueous solution was added dropwise to this reaction mixture, 20 mL of water and 45 mL of ethyl acetate (AcOEt) were subsequently added thereto and extraction with AcOEt was performed. The aqueous layer was extracted twice with 20 mL of AcOEt and combined organic layer was concentrated under reduced pressure. After 3 mL of ethanol was added to the concentrate to dissolve it, the solution was purified with an ODS column (YMC Dispo PackAT, mobile phase: acetonitrile aqueous solution) to give 0.7 g (2.39 mmol, HPLC purity: 100%) of α-lipoic acid trisulfide.

The HPLC conditions are as follows.

Detector: Ultraviolet absorptiometer (measurement wavelength: 220 nm)

Column: LiChrosorb RP-18 (Kanto Chemical Co., Inc., 4.0×250 mm, 5 μm)

Column temperature: Constant temperature around 40° C.

Mobile phase A: Phosphoric acid aqueous solution (pH 3)

Mobile phase B: Methanol

Mobile phase delivery: The mixing ratio of the mobile phase A and the mobile phase B is changed as follows to control the concentration gradient.

TABLE 4

| Time (minute) after injection | Mobile phase A (vol %) | Mobile phase B (vol %) |
|---|---|---|
| 0~5 | 100 | 0 |
| 5~15 | 100 → 25 | 0 → 75 |
| 15~20 | 25 | 75 |
| 20~21 | 25 → 100 | 75 → 0 |
| 21~30 | 100 | 0 |

Flow rate: 1.0 mL/min

Example 4

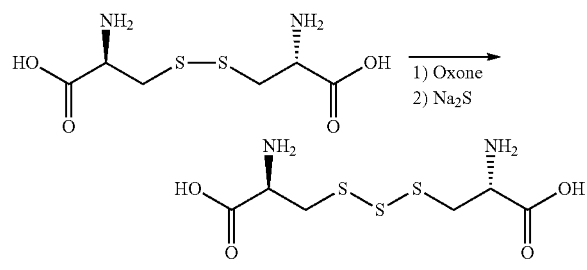

1.0 g (4.16 mmol) of L-cystine and 10 mL of a 1 mol/L sulfuric acid aqueous solution were added to a reaction container and cooled in an ice bath. 1.5 g (4.35 mmol) of Oxone (registered trademark) was added thereto to cause a reaction for about 1 hour. Subsequently, 1.1 g (4.37 mmol) of sodium sulfide nonahydrate was added thereto to cause a reaction for about 3 hours. After adding dropwise 19 mL of a 1 mol/L sodium hydrogen carbonate aqueous solution to a reaction mixture, the slurry was filtered and washed with 10 mL of water. The wet crystals collected by filtration were dried under reduced pressure at room temperature to give 0.75 g (2.75 mmol, HPLC purity: 89%) of cysteine trisulfide.

The HPLC conditions are the same as those described in Example 1.

Example 5

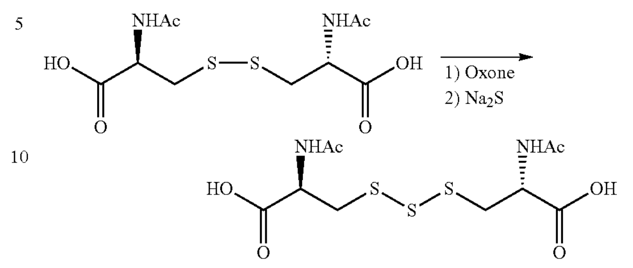

1.0 g (3.08 mmol) of N,N'-diacetyl-L-cystine and 10 mL of water were added to a reaction container, and the mixture was cooled to an internal temperature of 1° C. 1.25 g (3.72 mmol) of Oxone (registered trademark) was added thereto to cause a reaction for about 3 hours. Subsequently, 8.5 mL (3.71 mmol) of a 0.44 mol/L sodium sulfide aqueous solution was added dropwise thereto to cause a reaction for about 3 hours. After adding 33 mL of acetonitrile to the reaction mixture, inorganic salts were filtered and washed with 5 mL of acetonitrile. This filtrate was concentrated under reduced pressure with an evaporator, and the concentrate was purified with an ODS column (mobile phase: acetonitrile aqueous solution) to give 0.2 g (0.56 mmol) of N,N'-diacetyl-L-cysteine trisulfide.

The HPLC conditions are as follows.

Detector: Ultraviolet absorptiometer (measurement wavelength: 220 nm)

Column: LiChrosorb RP-18 (Kanto Chemical Co., Inc., 4.0×250 mm, 5 μm)

Column temperature: Constant temperature around 40° C.

Mobile phase: 40% (v/v) Acetonitrile aqueous solution

Flow rate: 0.5 mL/min

Example 6

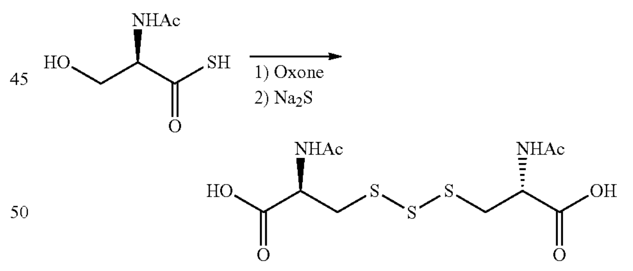

1.0 g (6.13 mmol) of N-acetyl-L-cystine and 40 mL of a 20% acetonitrile aqueous solution were added to a reaction container, and the mixture was cooled to an internal temperature of 5° C. 3.4 g (10.14 mmol) of Oxone (registered trademark) was added thereto to cause a reaction for about 2.5 hours. Subsequently, 1.5 g (6.12 mmol) of sodium sulfide nonahydrate was added thereto to cause a reaction for about 1 hour. After adding 33 mL of acetonitrile thereto, inorganic salts were filtered and washed with 3 mL of acetonitrile. This filtrate was concentrated under reduced pressure with an evaporator, and the concentrate was purified with an ODS column (mobile phase: acetonitrile aqueous solution) to give 0.1 g (0.28 mmol) of N,N'-diacetyl-L-cysteine trisulfide.

The HPLC conditions are the same as those described in Example 5.

Example 7

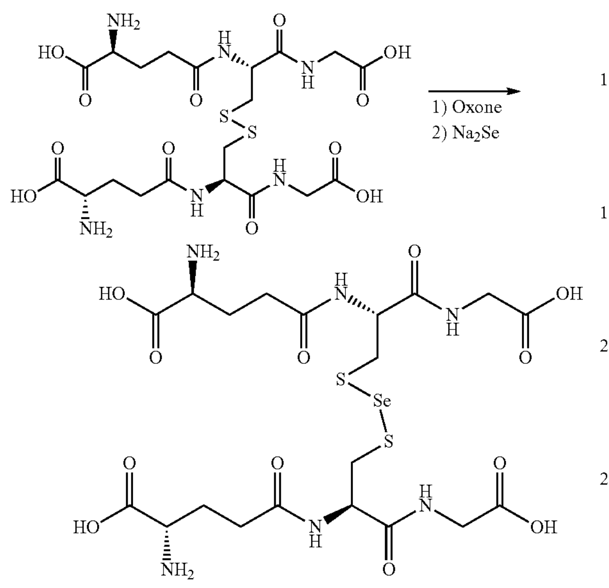

500.3 mg (0.69 mmol) of oxidized glutathione (GSSG) and 8.5 mL of a 0.2 mol/L sulfuric acid aqueous solution were added to a reaction container and cooled in an ice bath. 278.0 mg (0.83 mmol) of Oxone (registered trademark) was added thereto to cause a reaction for about 2.5 hours. Subsequently, 6 mL of a 1.0 mol/L sodium hydrogen carbonate aqueous solution was added dropwise thereto, and then 3.8 mL (0.76 mmol) of a 0.2 mol/L sodium selenide aqueous solution was added dropwise thereto to cause a reaction for about 1 hour. This reaction mixture was analyzed through LC/MS (HR-ESI-TOF-MS), and production of glutathione selenotrisulfide (GSSeSG) was confirmed. HR-ESI-TOF-MS m/z 691.0593 ($[M+H]^-$), calcd for $[C_{20}H_{31}N_6O_{12}S_2Se]^-$ 691.0607

Example 8

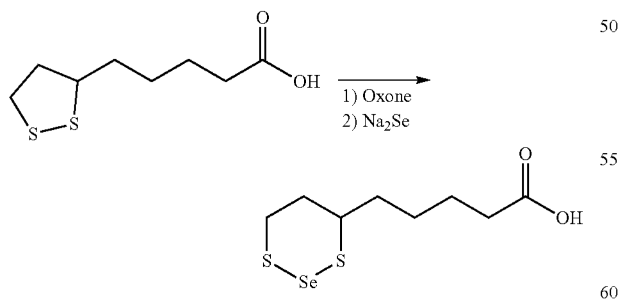

246.8 mg (1.20 mmol) of α-lipoic acid and 4.9 mL of a 75% ethanol aqueous solution were added to a reaction container, and the mixture was cooled in an ice bath. 419.1 mg (1.26 mmol) of Oxone (registered trademark) was added thereto to cause a reaction for about 1 hour. Inorganic salts in the reaction mixture were filtered and washed in 1 mL of ethanol. 2.6 mL of a 1.0 mol/L sodium hydrogen carbonate aqueous solution was added dropwise to the filtrate, and then 117 mg (0.93 mmol) of sodium selenide was added thereto to cause a reaction for about 3 hours. This reaction mixture was analyzed through LC/MS (HR-ESI-TOF-MS), and production of α-lipoic acid selenotrisulfide (α-lipoic acid SSeS) was confirmed.

HR-ESI-TOF-MS m/z 284.9522 ($[M+H]^-$), calcd for $[C_8H_{13}O_2S_2Se]^-$ 284.9514

The LC/MS conditions are as follows.

Detector: Photodiode array detector (measurement wavelength: 190 to 285 nm)
Mass spectrometer (ESI method, negative mode, m/z 100 to 1500)
Capillary voltage: 2.5 kV
Ion source temperature: 150° C.
Column: Meteoric Core C18 (YMC CO., LTD., 4.6×150 mm, 2.7 μm)
Column temperature: Constant temperature around 40° C.
Mobile phase A: 0.1% Formic acid aqueous solution
Mobile phase B: 0.1% Formic acid acetonitrile solution
Mobile phase delivery: The mixing ratio of the mobile phase A and the mobile phase B is changed as follows to control the concentration gradient.

TABLE 5

| Time (minute) after injection | Mobile phase A (vol %) | Mobile phase B (vol %) |
|---|---|---|
| 0~10 | 100 | 0 |
| 10~40 | 100 → 2 | 0 → 98 |
| 40~41 | 2 → 100 | 98 → 0 |
| 41~60 | 100 | 0 |

Flow rate: 0.5 mL/min

Retention time:
Example 7 GS(=O)SG (about 5 minutes), GSSG (about 12 minutes), and GSSeSG (about 16 minutes)
Example 8 Lipoic acid sulfoxide (about 25 minutes), α-lipoic acid (about 29 minutes), and α-lipoic acid selenotrisulfide (about 32 minutes)
Injection volume: 10 μL

The invention claimed is:

1. A method for producing a trisulfide compound or a selenotrisulfide compound, comprising:

oxidizing a disulfide compound with an oxidizing agent to obtain a sulfoxide compound; and allowing the obtained sulfoxide compound to react with a sulfur source or a selenium source to obtain a trisulfide compound or a selenotrisulfide compound, wherein obtaining the sulfoxide compound and obtaining the trisulfide compound or the selenotrisulfide compound are performed in a one-pot reaction, wherein the sulfur source is selected from the group consisting of sodium sulfide, potassium sulfide, sodium hydrosulfide, potassium hydrosulfide, and hydrogen sulfide, and the selenium source is selected from the group consisting of sodium selenide, potassium selenide, sodium hydroselenide, potassium hydroselenide, and hydrogen selenide, and wherein the disulfide compound is (1) a compound represented by $R^1$—S—S—$R^2$, wherein $R^1$ and $R^2$ may be the same or different, and each represents an alkyl group, each of which may be optionally substituted with one or more substituents selected from Substituent Group A, wherein Substituent Group A consists of a hydroxy group, an amino group optionally substituted with one or more substituents selected from Substituent Group B, and an oxo group, and Substituent Group B consists of an alkyl group optionally substituted with one or more substituents selected from the group consisting of a hydroxy group, an amino group, an oxo group, and an acetyl group, or (2) a compound represented by $R^3$—S—S—$R^4$, wherein $R^3$ and $R^4$ may be the same or different, and each represents a group in which an SH group is removed from cysteine optionally protected by a protective group or a group in which an SH group is removed from a cysteine-containing peptide optionally protected by a protective group.

2. The method according to claim 1, wherein the oxidizing agent is selected from the group consisting of potassium peroxymonosulfate, peracetic acid, hydrogen peroxide, hydrogen peroxide with methyltrioxorhenium, and sodium periodate.

3. The method according to claim 1, which is a method for producing a selenotrisulfide compound.

4. The method according to claim 1, which is a method for producing a trisulfide compound.

* * * * *